(12) United States Patent
Chinn

(10) Patent No.: US 6,799,466 B2
(45) Date of Patent: Oct. 5, 2004

(54) GUIDED ACOUSTIC WAVE INSPECTION SYSTEM

(75) Inventor: Diane J. Chinn, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 28 days.

(21) Appl. No.: 10/102,063

(22) Filed: Mar. 19, 2002

(65) Prior Publication Data

US 2002/0134161 A1 Sep. 26, 2002

Related U.S. Application Data

(60) Provisional application No. 60/278,353, filed on Mar. 22, 2001.

(51) Int. Cl.[7] .............................................. G01N 29/00
(52) U.S. Cl. .............................. 73/622; 73/628; 73/638
(58) Field of Search ........................ 73/622, 627, 628, 73/643, 599, 600, 602, 624, 597; 324/240, 220

(56) References Cited

U.S. PATENT DOCUMENTS

| | | | | |
|---|---|---|---|---|
| 4,685,334 A | * | 8/1987 | Latimer ........................ | 73/599 |
| 4,980,642 A | * | 12/1990 | Rodney ....................... | 324/325 |
| 5,359,898 A | * | 11/1994 | Latimer ........................ | 73/600 |
| 5,526,691 A | | 6/1996 | Latimer et al. | |
| 5,734,588 A | * | 3/1998 | Rose et al. ................... | 702/39 |
| 5,767,410 A | | 6/1998 | Lareau et al. | |
| 6,079,273 A | | 6/2000 | Latimer et al. | |
| 6,138,514 A | * | 10/2000 | Iwamoto et al. ............... | 73/622 |
| 6,148,672 A | * | 11/2000 | Cawley et al. ................. | 73/622 |
| 6,294,912 B1 | * | 9/2001 | Kwun .......................... | 324/240 |
| 6,360,609 B1 | * | 3/2002 | Wooh ........................... | 73/602 |
| 6,367,328 B1 | * | 4/2002 | Gorman et al. ............... | 73/592 |
| 6,373,245 B1 | * | 4/2002 | Kwun et al. ................. | 324/240 |
| 6,396,262 B2 | * | 5/2002 | Light et al. .................. | 324/240 |
| 6,424,150 B2 | * | 7/2002 | Kwun et al. ................. | 324/216 |
| 6,429,650 B1 | * | 8/2002 | Kwun et al. ................. | 324/240 |
| 6,575,043 B1 | * | 6/2003 | Huang et al. ............. | 73/861.25 |
| 6,595,059 B2 | * | 7/2003 | Gorman et al. ............... | 73/592 |
| 6,595,061 B2 | * | 7/2003 | Gorman et al. ............... | 73/597 |
| 6,622,561 B2 | * | 9/2003 | Lam et al. .................... | 73/622 |
| 2001/0017541 A1 | | 8/2001 | Kwun et al. | |

FOREIGN PATENT DOCUMENTS

| | | |
|---|---|---|
| EP | 0935258 A1 | 8/1999 |
| EP | 1061363 A2 | 12/2000 |
| EP | 1061364 A2 | 12/2000 |
| WO | WO 96 28727 A1 | 9/1996 |

OTHER PUBLICATIONS

Bauer, D. G., et al., et al., "Interpreting recovery boiler tube thickness data," Tappi Journal, vol. 79, No. 11, pp. 161–169, Nov. 1996.

Bauer, D. G., et al., "The inspection of recovery boilers to detect factors that cause critical leaks," Tappi Journal, pp. 92–100, Sep. 1991.

* cited by examiner

*Primary Examiner*—Hezron Williams
*Assistant Examiner*—Jacques M. Saint-Surin
(74) *Attorney, Agent, or Firm*—Eddie E. Scott; Alan H. Thompson

(57) ABSTRACT

A system for inspecting a conduit for undesirable characteristics. A transducer system induces guided acoustic waves onto said conduit. The transducer system detects the undesirable characteristics of the conduit by receiving guided acoustic waves that contain information about the undesirable characteristics. The conduit has at least two sides and the transducer system utilizes flexural modes of propagation to provide inspection using access from only the one side of the conduit. Cracking is detected with pulse-echo testing using one transducer to both send and receive the guided acoustic waves. Thinning is detected in through-transmission testing where one transducer sends and another transducer receives the guided acoustic waves.

5 Claims, 1 Drawing Sheet

GUIDED ACOUSTIC WAVE INSPECTION SYSTEM

CROSS-REFERENCE TO RELATED APPLICATIONS

This application claims the benefit of U.S. Provisional Application No. 60/278,353, filed Mar. 22, 2001, and titled, "Guided Acoustic Wave Inspection System for Kraft Recovery Boiler Tubing." U.S. Provisional Application No. 60/278,353, filed Mar. 22, 2001, titled, "Guided Acoustic Wave Inspection System for Kraft Recovery Boiler Tubing," is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to inspection systems and more particularly to acoustic wave inspection systems.

2. State of Technology

U.S. Pat. No. 6,079,273 for EMAT inspection of header tube stubs by Paul J. Latimer, assigned to McDermott Technology, Inc. and The Babcock & Wilcox Company, patented Jun. 27, 2000, provides the following description, "A method for non-destructively testing closely-spaced objects, such as header tube stubs for a furnace or boiler using electromagnetic acoustic transducers (EMATs) having meander coil sensors. The small size of the sensor combined with the need to move the sensor only a small fraction of the circumference of a tube to scan the entire circumference of the tube under test permits easy and accurate testing of an entire tube, even when the tube is one of a closely-spaced bundle."

U.S. Pat. No. 5,359,898 for hydrogen damage confirmation with EMATs by Paul J. Latimer, assigned to The Babcock & Wilcox Company, patented Nov. 1, 1994, provides the following description, "A method and apparatus for use in confirming hydrogen damage in a boiler tube comprises a pair of electromagnetic acoustic transducer coils which are mounted for movement toward and away from each other. An electromagnet produces pulses that generate acoustic beams across a chord and within the wall thickness of the boiler tube. For adapting to boiler tubes of different outside diameters, the transducers coils are mounted on a resilient member so that the coils can be pressed against the outer surface of coils having a variety of outside diameters. The angle of the acoustic beam between the coils must also be adjusted, however, and this is done by changing the frequency of energy applied to the coils."

U.S. Pat. No. 6,148,672 for inspection of pipes by Peter Cawley, et al., assigned to Imperial College of Science, Technology of Medicine, patented Nov. 21, 2000, provides the following description, "An apparatus and a method for inspecting elongate members, especially pipes, using Lamb waves. The apparatus and method provide for the propagation of an axi-symmetric Lamb wave of a single mode in one direction along the pipe. A receiver is provided to receive the Lamb wave after its passage along the pipe and convert the received wave for storage, processing and analysis to determine whether or not there are faults present in the pipe. The apparatus includes at least one and usually several excitation rings each having a plurality of Lamb wave exciters deployed in equiangular spacing in a ring clamping structure whereby each exciter can be pressed with equal force against the surface of the pipe under inspection."

U.S. Pat. No. 5,767,410 for Lamb wave ultrasonic probe for crack detection and measurement in thin-walled tubing by John P. Lareau, et al., assigned to Combustion Engineering, Inc., patented Jun. 16, 1998, provides the following description, "A probe inspects steam generator tubing for defects. The probe includes a transducer which generates a localized ultrasonic Lamb wave. The ultrasonic wave is transferred to the tubing by a coupling medium, such as water, that physically couples the transducer and the tubing. Defects in the tubing reflect the ultrasonic wave to the probe which detects the reflections. The results are then used to determine the length and depth of such defects as cracks, pitting, and thinning. The localized ultrasonic wave performs an inspection sensitive enough to detect ligaments between crack segments. This allows highly accurate predictions of tubing integrity and rupture strength."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a system for inspecting conduits such as tubes, pipes, etc., for undesirable characteristics. The system includes a transducer system that induces guided acoustic waves onto said conduit and detects defects. The transducer system induces guided acoustic waves in the conduit and detects the undesirable characteristics of the conduit by receiving guided acoustic waves that contain information about the undesirable characteristics. The conduit has at least two sides and the transducer system utilizes torsional modes of propagation to provide inspection using access from only the one side of the conduit. Cracking is detected with pulse-echo testing using one transducer to both send and receive the guided acoustic waves. Thinning is detected in through-transmission testing where one transducer sends and another transducer receives the guided acoustic waves.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
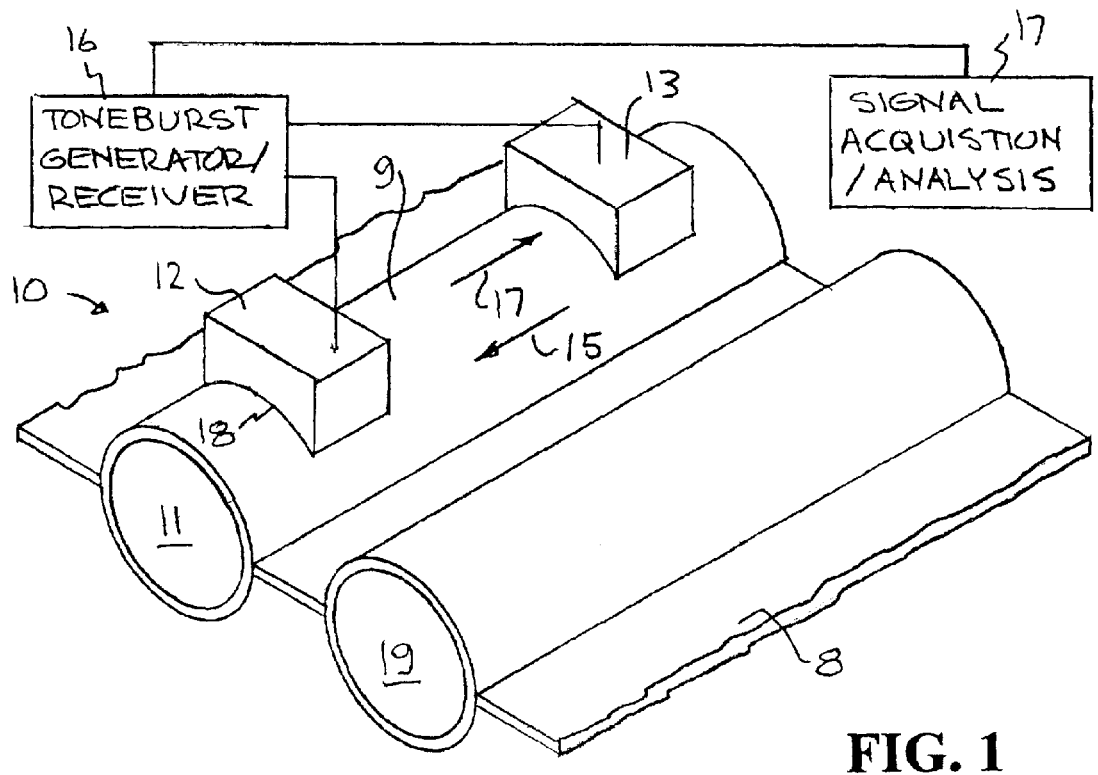
FIG. 1 illustrates an embodiment of a system for inspecting a conduit.

Referring now to the drawings, to the following detailed information, and to incorporated materials; a detailed description of the invention, including specific embodiments, is presented. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

There is a significant need for improved systems for inspecting conduits such as pipes, tubes, ducts, etc. One example of the need for a system for inspecting a conduit is in Kraft recovery boilers. In pulp and paper industry Kraft recovery boilers, water-filled tubes constitute the structure of the furnace serving to absorb thermal energy from the furnace. Exposed to combustion on the fireside and filled with pressurized flowing feedwater, recovery boiler wall tubes must withstand large and variable thermal and mechanical stresses. Furnace gas temperatures up to 2500° F. combined with the harsh molten salt environment can cause premature corrosion on the outer diameter and erosion on the inner diameter of the recovery boiler wall tubes.

There are many examples of the need for an inspection system. For example in the electric power industry and nuclear power industry tubes need inspection. Also, inspection is needed in sanitary sewers. Sanitary sewer overflows often pose problems in deteriorating sewer systems. The U.S. Environmental Protection Agency (EPA) is proposing to clarify and expand permit requirements for 19,000 municipal sanitary sewer collection systems in order to reduce sanitary sewer overflows. The proposed Sanitary Sewer Overflows Rules will help communities improve some of the Nation's most valuable infrastructure—our wastewater collection systems—by requiring facilities to develop and implement new capacity, management, operations, maintenance and public notification programs.

The EPA regulations are expected to have a significant impact on collection system owners and the way in which sewer systems are managed. Properly designed, operated, and maintained sanitary sewer systems are meant to collect and transport all of the sewage that flows into them to a publicly owned treatment works. However, occasional unintentional discharges of raw sewage from municipal sanitary sewers occur in almost every system. These types of discharges are called sanitary sewer overflows. Sanitary sewer overflows have a variety of causes, including but not limited to severe weather, improper system operation and maintenance, and vandalism. EPA estimates that there are at least 40,000 sanitary sewer overflows each year. The untreated sewage from these overflows can contaminate waters, causing serious water quality problems. It can also back-up into basements, causing property damage and threatening public health.

Deteriorating underground sewer infrastructure is generally not readily identifiable. Failures of sewer lines are often not known until they become an emergency. For example, a robot for the repair of sewer pipes is shown in U.S. Pat. No. 6,101,951 for by Alwin Sigel, patented Aug. 15, 2000. U.S. Pat. No. 6,101,951 states that "The use of robots in the repair of sewer pipes which are not man-sized is already known. Such robots, which are provided with a drive means for moving them through sewer pipes, are suitable, e.g., for the cleaning of sewer pipes, for grinding off irregularities or protrusions or for the mending of leaks. A known multi-segment robot for the above purposes is provided with a rotary head carrying a plurality of treatment tools and a camera. By means of a rotary motor, the rotary head and the robot arm connected thereto can be rotated in a controlled manner by up to 500 degrees about the longitudinal axis. Behind the rotary motor, which is supported on the sewer pipe wall by support wheels, a switch and relay unit is arranged for controlling the functions of the motor. If, for instance, the robot is used to fill leaks or other gaps, a press-out container will be arranged behind the switch and relay unit. The material to be applied is pressed via a hose from the press-out container to the tool arranged on the rotary head and thus can be applied by the tool. Arranged behind the press-out container is a carriage unit for moving the multi-segment robot through the sewer pipe under treatment. For this purpose, the carriage, serving as a tractor, comprises a plurality of wheels driven by a traction motor." The disclosure of U.S. Pat. No. 6,101,951 is incorporated herein by reference.

The present invention provides a system for inspecting a conduit for undesirable characteristics. The system includes a transducer system that induces guided acoustic waves onto said conduit and detects defects. The transducer system induces guided acoustic waves in the conduit and detects the undesirable characteristics of the conduit by receiving guided acoustic waves that contain information about the undesirable characteristics. The conduit has at least two sides and the transducer system utilizes flexural modes of propagation to provide inspection using access from only the one side of the conduit. Cracking is detected with pulse-echo testing using one transducer to both send and receive the guided acoustic waves. Thinning is detected in through-transmission testing where one transducer sends and another transducer receives the guided acoustic waves.

One example of use of a system for inspecting a conduit will now be described. In pulp and paper industry Kraft recovery boilers, water-filled tubes constitute the structure of the furnace serving to absorb thermal energy from the furnace. Exposed to combustion on the fireside and filled with pressurized flowing feedwater, recovery boiler wall tubes must withstand large and variable thermal and mechanical stresses. Furnace gas temperatures up to 2500° F. combined with the harsh molten salt environment can cause premature corrosion on the outer diameter and erosion on the inner diameter of the recovery boiler wall tubes.

Extensive damage to recovery boiler tubes can result in a significant safety and environmental hazard. Industry-wide, there have been smelt water explosions resulting from boiler tubes leaking water into the furnace. An explosion of this type can lead to serious injury or loss of life. In addition, smelt water explosions have the potential of releasing objectionable gases and materials to the environment. Economically, plant downtime and cleanup costs resulting from smelt water explosions are extremely high. In addition, critical leaks in tubing account for boiler shutdowns industry-wide.

The system of the present invention addresses the effectiveness, effort and time currently required to inspect tubing in Kraft recovery boilers used in the pulp and paper industry. Currently, inspection for tube thinning is performed using ultrasonic thickness measurements at spatial intervals throughout the boiler. Inspection for tube cracks is done visually and may be followed up with ultrasonic inspection or dye penetrant testing. Tube inspection is performed during annual maintenance and takes approximately 9 days, including the time to build and take down scaffolding and the time to clean the tubing for inspection. Shutdown time of a recovery boiler costs the owner a significant amount in lost revenue. In the Kraft recovery boiler, water-filled tubes constitute the structure of the furnace serving to absorb thermal energy from the furnace. Exposed to combustion on the fireside and filled with pressurized flowing feedwater, recovery boiler wall tubes must withstand large and variable thermal and mechanical stresses. Furnace gas temperatures up to 2500° F. combined with the harsh molten salt environment can cause premature corrosion on the outer diameter and erosion on the inner diameter of the recovery boiler wall tubes.

Considerable plant resources are expended to inspect recovery boiler tubing. Currently, visual and ultrasonic inspection are primarily used during the annual maintenance shutdown to monitor corrosion rates and cracking of tubing. Visual inspection for cracking and thinning is targeted at suspicious areas. During each maintenance shutdown, ultrasonic thickness measurements are taken at discrete locations according to a grid pattern. Comparison of thickness data at specific locations to thickness from preceding years yields a corrosion rate. Because of the variability in ultrasonic thickness measurements, average corrosion rates of 0.006"/yr have standard precision error of 0.005" to 0.007". Replacement of tubing usually occurs according to the corrosion rates determined by ultrasonic measurements.

Referring now to FIG. 1, a system for inspecting a conduit is illustrated. The embodiment is designated generally by the reference numeral 10. In the present invention, guided acoustic waves are used to detect in-service defects. A piezoelectric or electromagnetic transducer generates a guided wave. Defect type and tube geometry determines the appropriate guided wave mode. The system 10 for inspecting a conduit has particular benefit in the inspection of pulp and paper Kraft recovery boiler tubing. The detailed description of the specific embodiments, together with the general description of the invention, serves to explain the principles of the invention.

The system 10 for inspecting a conduit is illustrated as an embodiment of a guided wave corrosion detection system for Kraft recovery boiler tubing. Guided acoustic waves have been developed as an inspection technique for tubular members. This acoustic technique is cost-effective in inspecting long lengths of tubes from a single inspection point. Guided acoustic waves can inspect entire cross-sections of tubes of significant length, including the areas around bends in tubes. Torsional modes of propagation allow inspection of the entire cross-section using access from only one side of the tube. This technique appears very promising for recovery boiler tube application by expediting annual inspection and providing online periodic monitoring of tube integrity. Development of a sensor for monitoring the integrity of recovery boiler tubes during the lifetime of the furnace allows timely replacement of cracked or corroded tubes.

Guided waves, or Lamb waves, are two-dimensional acoustic waves that propagate in packets in plate-type members. Material in the entire cross-section of a member is excited in a toneburst mode. Because the cross-section is coherently excited, guided waves in tubular sections can travel long distances in structures and are generally unaffected by insulation or bends in the tube. With certain modes of propagation, these acoustic waves change characteristically with the type and extent of damage in a cross-section. These features make guided waves an attractive method for inspection of conduits such as tubes and pipes.

Guided waves provide a means of inspecting large areas of a structure from a single inspection point. With guided waves, large sections of a single tube in the recovery boiler, including the fireside, can be inspected from a single access point on the cold side. Damage location is identified by the travel time of wave propagation.

Furnace environments present several challenges to current guided wave inspection techniques. Some of the challenges include generation of guided waves using sensors that operate at high temperatures, determining the sensitivity of guided waves to the types of defects expected, and assessing thermal and mechanical effects of the furnace environment on guided wave propagation.

The system 10 for inspecting a conduit when applied to defect monitoring of boiler tubes is expected to have considerable economic, environmental and safety benefits for the industry. Benefits of a guided wave monitoring system include reducing smelt water explosion hazard and decreasing annual maintenance shutdown time. Periodic monitoring of the tubes will reduce environmental and safety hazards by characterizing growth of corrosion/erosion and crack defects and allow timely replacement of tubing to prevent catastrophic failure by smelt water explosion. Monitoring defects can decrease the risk of serious injury or loss of life due to explosion. For example, elimination of 2 explosions per year, each resulting in a three-week shutdown would save the industry a substantial amount in annual shutdown and repair costs.

Early detection and tracking of incipient corrosion/erosion and cracking will allow the tubes to be replaced economically, during normal scheduled maintenance instead of during costly unscheduled outages. Because guided wave testing looks at the entire cross-section of the tube instead of at specific locations as in ultrasonic thickness measurements, more reliable data result. Implementation of a monitoring system can both guide inspectors to problematic areas and decrease the inspection time in areas that show no evidence of defects.

Using the system 10 for inspecting a conduit when applied to defect monitoring of boiler tubes, annual maintenance shutdown time could be reduced. A decrease of 2 days during annual maintenance shutdown at 25 plants can result in estimated yearly savings of approximately $48 million to the industry.

Referring again to FIG. 1, the system 10 for inspecting a conduit is illustrated as an embodiment of a guided wave corrosion detection system for Kraft recovery boiler tubing. One tube 11 of the Kraft recovery boiler tubing is shown being inspected. Guided acoustic waves have been developed as an inspection technique for tubular members. Guided waves are excited in the tubing 11 with one or more piezoelectric or electromagnetic transducers 12 and 13. The transducer 12 is a send/receive traducer and the transducer 12 is a receive traducer.

A feature of this system 10 is its cost-effectiveness in inspecting long lengths of tubes or inaccessible tubes from a single inspection point. Flexural modes of propagation allow inspection of the entire cross-section using access from only one side of the tube 11. This is advantageous for recovery boiler tubing application because it can expedite annual inspections, offer a more accurate assessment of tube conditions, and provide on-line periodic monitoring of tube integrity.

Modeling and experiment determine the propagation mode with the most sensitivity to the type of defect under inspection. A single length of tubing 11 can be inspected. Wall thinning is tested in through-transmission with two transducers 12 and 13 inspecting the included tubing distance. A change in the propagation mode indicates thinning. Cracks are detected in pulse-echo mode with one transducer 12 both sending a mode and receiving a reflected mode. A crack can be located by the arrival time of its reflection. A reflection from a location other than a support or known discontinuity indicates a crack. Fireside tube conditions can be assessed from both the fireside and the coldside. With coldside high temperature probes, on-line monitoring of tubes can be achieved.

Identification of thinning or cracks by guided waves is intended as a screen for more detailed inspection. By performing large-scale inspection in less time than current techniques, guided waves offer a way to direct inspection efforts at specific problem areas. Instead of relying on an inspection grid to track thinning, 100% of the tubing between transducers is inspected. This technique gives inspectors an accurate assessment of tube conditions. When used on-line, guided waves can assess the rate of thinning and cracking and can be used to mitigate disastrous smelt-water explosions resulting from leaking tubes.

The system of the present invention uses guided waves to detect thinning and cracking in recovery boiler tubing. The system 10 can be used with membranes between tubes or on tangent tubing. Guided waves can be generated from partial circumferential loading of the tube 11. Flexural modes, readily generated with partial circumferential loading, are used in testing. Calculated dispersion curves define modes of propagation in the tubes. A flexural mode is chosen which is sensitive to either cracking or thinning. For recovery boiler tubing, propagation frequencies of the modes range from 10 kHz to 2 MHz in the system 10.

The piezoelectric or electromagnetic transducer 12 induces guided waves into the tubes. A toneburst generator 16 is used to excite the transducer 12, sweeping a range of frequencies. The transducer 12 detects fireside defects from the coldside or fireside of the tube. Fireside testing would be used during shutdown maintenance; coldside testing would be used while the boiler is in service or when the interior is inaccessible. A piezoelectric transducer is used for cold testing, a high-temperature electromagnetic transducer is used for in service testing. Cracking is detected with pulse-echo testing, using one transducer to both send and receive a reflected wave. Thinning is detected in through-transmission testing where one transducer sends and another transducer receives the guided wave. The signal acquisition/analysis electronics 17 is used to activate and control the system 10.

The transducers 12 and 13 are set so that the system 10 can inspect the entire cross-sections of continuous tubes, including the areas around bends in tubes. Torsional modes of propagation allow inspection of the entire cross-section using access from only one side of the tube. Guided waves are generated from partial circumferential loading of the tube 11. The tube 11 has a coldside and a fireside. The upper portion 9 of tube 11 will be considered the coldside in the illustrated example. The fireside is below the upper portion. Flexural modes are readily generated with partial circumferential loading and testing. Calculated dispersion curves define modes of propagation in the tubes. The system 10 can be used with membranes 8 between tubes. The membrane 8 is shown between tubes 11 and 19. A flexural mode is chosen which is sensitive to either cracking or thinning. For recovery boiler tubing, propagation frequencies of the modes range from 10 kHz to 2 MHz in the system 10.

The transducers 12 and 13 can be connected to tube 11 on only one portion 9 and still inspect the entire cross-sections of the tube 11. For example, transducer 12 has a recess 18 that fits over the surface of the portion 9 of tube 11. The piezoelectric or electromagnetic transducer 12 induces guided waves into the tubes. The transducer 12 can be operated in a toneburst mode. A toneburst generator 16 is used to excite the transducer 12, sweeping a range of frequencies. The transducer 12 detects fireside defects from the coldside or fireside of the tube. Fireside testing would be used during shutdown maintenance; coldside testing would be used while the boiler is in service or when the interior is inaccessible.

A system 10 provides inspection of a conduit for undesirable characteristics. A transducer system induces guided acoustic waves in the conduit and detects the undesirable characteristics of the conduit by receiving guided acoustic waves that contain information about the undesirable characteristics. The conduit has at least two sides and the transducer system utilizes flexural modes of propagation to provide inspection using access from only the one side of the conduit. Cracking is detected with pulse-echo testing using one transducer to both send and receive the guided acoustic waves. Thinning is detected in through-transmission testing where one transducer sends and another transducer receives the guided acoustic waves.

There are numerous embodiments of the system 10. In one embodiment the conduit has a separate side and the transducer system utilizes torsional modes of propagation of the guided acoustic waves to provide inspection of the entire cross-section of the conduit using access from only the one side of the conduit. In one embodiment the conduit has one side and the transducer system utilizes flexural modes of propagation to allow inspection using access from only the one side of the conduit. In one embodiment the conduit has a fireside and a cold side and the transducer system utilizes torsional modes of propagation of the guided acoustic waves to provide inspection of the entire cross-section of the conduit using access from only the cold side of the conduit.

In one embodiment the conduit has a fireside and a cold side and the transducer system induces guided waves into the conduit and detects fireside defects from the coldside or fireside of the conduit. In one embodiment the transducer system induces two-dimensional guided acoustic waves in the conduit that propagate in packets in plate-type members. The transducer system operates in a toneburst mode. In one embodiment the transducer system utilizes propagation frequencies of from 10 kHz to 2 MHz. In one embodiment the transducer system is a piezoelectric transducer. In one embodiment the apparatus includes a toneburst generator exciting the transducer, sweeping a range of frequencies. In one embodiment cracking in the conduit is detected with pulse-echo testing using one transducer to both send and receive the guided acoustic waves. In one embodiment thinning in the conduit is detected in through-transmission testing where one transducer sends and another transducer receives the guided acoustic waves. In one embodiment the transducer system is an electromagnetic transducer. In one embodiment the transducer system induces guided acoustic waves in the conduit and the guided acoustic waves are reflected from the undesirable characteristics, and the transducer system receives the guided acoustic waves reflected from the undesirable characteristics. In one embodiment the transducer system includes a first unit that induces guided acoustic waves in the conduit and the guided acoustic waves interact with the undesirable characteristics, and a second unit that receives the guided acoustic waves that have interacted with the undesirable characteristics. In one embodiment the transducer system utilizes changes in group velocity of the guided acoustic waves. In one embodiment the transducer system utilizes changes in mode conversions of the guided acoustic waves. In one embodiment the transducer system utilizes changes in transmission coefficients of the guided acoustic waves.

Figure 2:
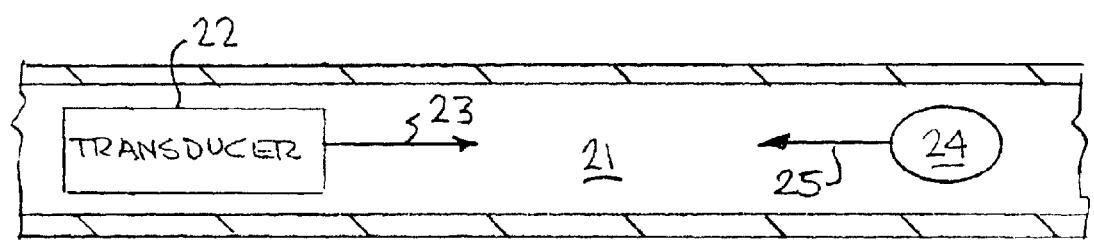
FIG. 2 illustrates an embodiment of the present invention wherein one transducer is used to both send and receive a reflected wave.

Referring now to FIG. 2, an embodiment of the present invention is illustrated wherein one transducer is used to both send and receive a reflected wave. The embodiment is designated generally by the reference numeral 20. The system 20 for inspecting a conduit is illustrated as an embodiment of a guided wave corrosion detection system for Kraft recovery boiler tubing. One tube 21 of the Kraft recovery boiler tubing is shown being inspected. Guided waves are excited in the tubing 21 with one piezoelectric or electromagnetic transducers 22. A piezoelectric transducer is used for cold testing and a high-temperature electromagnetic transducer is used for in-service testing. The transducer 22 sends a guided wave mode that propagates along the length of the pipe 21. The wave 23 then reflects from any flaws, such as corrosion 24, and returns to the transducer 22, which generated the wave 24. The reflection is illustrated by reflection wave 25. Using the system 20, cracking is detected with pulse-echo testing, using one transducer 22 to both send a wave 23 and receive a reflected wave 25. The advantage of system 20 is its cost-effectiveness in inspecting long lengths of tubes from a single inspection point. Flexural modes of propagation allow inspection of the entire cross-section using access from only one side of the tube 21.

Figure 3:
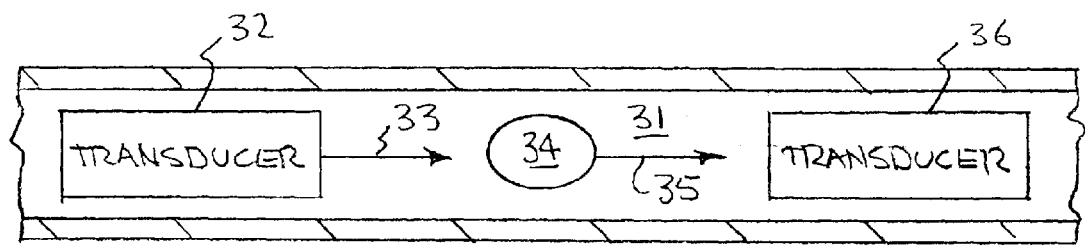
FIG. 3 illustrates an embodiment of the present invention wherein one transducer sends and another transducer receives a guided wave.

Referring now to FIG. 3, an embodiment of the present invention is illustrated wherein one transducer sends and another transducer receives a guided wave. The embodiment is designated generally by the reference numeral 30. The system 30 for inspecting a conduit is illustrated as an embodiment of a guided wave corrosion detection system for Kraft recovery boiler tubing. One tube 31 of the Kraft recovery boiler tubing is shown being inspected. Guided waves are excited in the tubing 31 with two or more piezoelectric or electromagnetic transducers 32 and 36. Piezoelectric transducers are used for cold testing and high-temperature electromagnetic transducers are used for in service testing. The transducer 32 sends a guided wave 33 mode that propagates along the length of the pipe 31. The guided wave 33 interacts with corrosion area 34. The corrosion will influence characteristics of the resulting waveform 35, which is received at the receiving transducer 36. Changes in group velocity, mode conversions, and transmission coefficients can be used to assess the damage. The advantage of system 30 is its cost-effectiveness in inspecting long lengths of tubes from a single inspection point. Flexural modes of propagation allow inspection of the entire cross-section using access from only one side of the tube 31. The system 30 for inspecting a conduit is used for detecting thinning with through-transmission testing where one transducer sends and another transducer receives the guided wave.

The present invention provides a system for inspecting a conduit for undesirable characteristics. It includes a number of steps. In one embodiment the steps include inducing guided acoustic waves in the conduit and detecting the undesirable characteristics of the conduit by receiving guided acoustic waves. In one embodiment cracking is detected with pulse-echo testing using one transducer to both send and receive the guided acoustic waves. In one embodiment thinning is detected in through-transmission testing where one transducer sends and another transducer receives the guided acoustic waves. In one embodiment the step of inducing guided acoustic waves is conducted in a toneburst mode. In one embodiment the step of inducing guided acoustic waves utilizes propagation frequencies of from 10 kHz to 2 MHz. In one embodiment the guided acoustic waves are induced in the conduit and the guided acoustic waves are reflected from the undesirable characteristics. In one embodiment the guided acoustic waves are induced in the conduit and the guided acoustic waves interact with the undesirable characteristics. In one embodiment changes in group velocity of the guided acoustic waves are utilized. In one embodiment changes in mode conversions of the guided acoustic waves are utilized. In one embodiment changes in transmission coefficients of the guided acoustic waves are utilized.

In one embodiment torsional modes of propagation of the guided acoustic waves are utilized to provide inspection of the entire cross-section of the conduit using access from only the one side of the conduit. In one embodiment the conduit has one side and the system utilizes flexural modes of propagation to allow inspection using access from only the one side of the conduit. In one embodiment the conduit has a fireside and a cold side and the system utilizes torsional modes of propagation of the guided acoustic waves to provide inspection of the entire cross-section of the conduit using access from only the cold side of the conduit. In one embodiment the conduit has a fireside and a cold side and the system induces guided waves into the conduit and detects fireside defects from the coldside or fireside of the conduit. In one embodiment a toneburst generator provides a sweeping range of frequencies. In one embodiment cracking in the conduit is detected with pulse-echo testing using a single transducer to both send and receive the guided acoustic waves. In one embodiment thinning in the conduit is detected in through-transmission testing where a first transducer sends and a second transducer receives the guided acoustic waves.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. An apparatus for inspecting Kraft recovery boiler tubing for fireside defects, the Kraft recovery boiler tubing including a tubular conduit, a portion with an axial length, a fireside, a cold side, and a membrane connecting the tubular conduit with the Kraft recovery boiler tubing, for undesirable characteristics, comprising:

a transducer system, said transducer system including a first piezoelectric transducer that induces guided waves in the tubular conduit from the cold side.

a toneburst generator that induces two-dimensional Lamb waves that propagate in packets in a sweeping a range of frequencies from 10 kHz to 2 MHz in said conduit, said first piezoelectric transducer having means for partial circumferential loading of said first piezoelectric transducer external to the fireside of said tubular conduit and on the cold side of said tubular conduit and above the membrane connecting the tubular conduit with the Kraft recovery boiler tubing, a second piezoelectric transducer spaced from said first piezoelectric transducer along the axial length of the portion of the tubular conduit that detects the fireside defects of said conduit by receiving said two-dimensional Lamb waves that contain information about the fireside defects, said second piezoelectric transducer having means for circumferential loading of said second piezoelectric transducer external to the fireside of said tubular conduit and on the cold side of said tubular conduit and above the membrane connecting the tubular conduit with the Kraft recovery boiler tubing.

2. The apparatus of claim 1 wherein said toneburst generator induces two-dimensional Lamb waves in said tubular conduit from the cold side of the tubular conduit and said two-dimensional Lamb waves interact with the fireside defects in said tublar conduit located in the fireside of the tubular conduit and said second piezoelectric transducer receives said two-dimensional Lamb waves that have interacted with the fireside defects.

3. The apparatus of claim 1 wherein said transducer system utilizes changes in group velocity of said two-dimensional Lamb waves.

4. The apparatus of claim 1 wherein said transducer system utilizes changes in mode conversions of said two-dimensional Lamb waves.

5. The apparatus of claim 1 wherein said transducer system utilizes changes in transmission coefficients of said two-dimensional Lamb waves.

* * * * *